United States Patent [19]

Lorenz

[11] Patent Number: 5,421,833
[45] Date of Patent: Jun. 6, 1995

[54] HAIR DYE COMPOSITIONS BASED ON OXIDATION DYESTUFF PRECURSORS

[75] Inventor: Heribert Lorenz, Gross-Bieberau, Germany

[73] Assignee: Goldwell AG, Germany

[21] Appl. No.: 180,367

[22] Filed: Jan. 12, 1994

[30] Foreign Application Priority Data

Jan. 22, 1993 [DE] Germany .................. 43 01 663.4

[51] Int. Cl.$^6$ .............................................. A61K 7/13
[52] U.S. Cl. .................................... 8/410; 8/406; 8/408; 8/409; 8/411; 8/412; 8/416
[58] Field of Search ............... 8/405, 406, 408, 410, 8/411, 412, 409, 416

[56] References Cited

U.S. PATENT DOCUMENTS

| | | | |
|---|---|---|---|
| 3,884,627 | 5/1975 | Brody et al. | 8/410 |
| 3,970,423 | 7/1976 | Brody et al. | 8/410 |
| 4,125,367 | 11/1978 | Bugaut et al. | 8/411 |
| 4,402,700 | 9/1983 | Feinland et al. | 8/416 |
| 4,532,127 | 7/1985 | Feinland et al. | 8/406 |
| 4,745,652 | 5/1988 | Rose et al. | 8/409 |
| 5,096,455 | 3/1992 | Grollier | 8/410 |
| 5,167,669 | 12/1992 | Grollier | 8/405 |

FOREIGN PATENT DOCUMENTS

| | | |
|---|---|---|
| 0146350 | 6/1985 | European Pat. Off. . |
| 0414585 | 2/1991 | European Pat. Off. . |
| 2240495 | 4/1973 | Germany . |

*Primary Examiner*—Christine Skane
*Assistant Examiner*—Caroline L. Dusheck

[57] ABSTRACT

Hair dye compositions without sensitizing potential but with improved dyeing properties for all shades comprise only 2-(2'-hydroxyethylamino)5-aminotoluene or the salts thereof as developing agent, or preferably in combination with the usual coupling agents, excluding 1-methoxy-2,4-diaminobenzene and 1-ethoxy-2,4-diaminobenzene.

6 Claims, No Drawings

HAIR DYE COMPOSITIONS BASED ON OXIDATION DYESTUFF PRECURSORS

The present invention refers to a hair dye composition on the basis of oxidation dyestuff precursors which are mixed with a peroxide-containing compound immediately before application and which include at least one developing agent as well as at least one coupling substance.

Furthermore, the invention comprises the use of a particular N-hydroxyethyl amino toluene as developing agent in those hair dyeing compositions which do not comprise any coupling substance.

It is well-known that hair dye compositions usually comprise two compounds which are kept separate until application; one of both contains oxidation dyestuff precursors, so-called developing agents and coupling substances and, in some cases, shade modifiers such as direct dyes, and the other compound, which is mixed with the first compound before application onto the hair, contains a peroxide, normally hydrogen peroxide. These dyestuffs lead to a permanent coloration of the hair.

Many substances have already been suggested as developing agents; these are predominantly various derivatives of 1,4-diaminobenzene. In practice, however, p-phenylenediamine on its own and p-toluylenediamine are predominantly used as developing agents; certain significance is also attributed to tetraaminopyrimidine.

These compositions still need to be improved regarding their dermatological properties, particularly their sensitizing effect, as well as the dyeing properties achieved therewith.

Surprisingly, it has now been found that hair dyeing compositions based on a developing/coupling system, which practically have no sensitizing potential but achieve improved coloring properties over the range of all conceivable shades, are obtained if 2-(2'-hydroxyethylamino)-5-aminotoluene or the salts thereof are used in combination with at least one coupling substance, whereby the precence of 1-methoxy-2,4-diaminobenzene or 1-ethoxy-2,4-diaminobenzene is excluded.

Moreover, it has been found that also 2-(2'-hydroxyethylamino)-5-aminotoluene on its own, of the formula

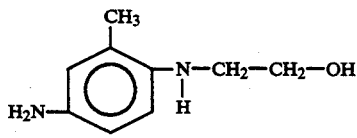

shows a coupling effect with itself and may therefore be used, also without any further coupling substances, optionally in admixture with further developing agents known per se, in oxidation dyestuff precursors which are suitable for hair dyeing after mixture with peroxides.

N-hydroxyethyl aminotoluenes per se are known substances. The preparation of the compound according to the invention may be performed in a generally known process, e.g., as covered by Example 5 of German Patent Application 2,240,495, reacting the appropriate p-aminonitrotoluene with 2-chloroethanol and subsequent hydrogenation.

2-(2'-hydroxyethyl)amino-5-toluene or the salts thereof, particularly the hydrochloride or sulfate, used as developing agent in oxidation hair dye compositions according to the invention may be used in admixture with any possible coupling substances, excluding 1-methoxy-2,4-diaminobenzene and 1-ethoxy-2,4-diaminobenzene which are not suitable to achieve the effects according to the invention, and which are also totally obsolete for toxicological reasons.

Therefore, the compositions described in European Patent Application No. 146,350 do not give any indication to the invention, because the N-(2-hydroxyethyl)-methyl-p-phenylendiamine derivatives described therein are solely used in combination with such coupling substances excluded herein.

European Patent Application No. 414,585 discloses hair dyeing compositions comprising a p-phenylenediamine derivative with a secondary amino group and an indole dyestuff, preferably 5,6-dihydroxyindole. The combination described therein is said to enable hair dyeing by the effect of atmospheric oxygen excluding the presence of an oxidizing agent, and therefore has no close connection to the present invention in respect of the problem and the solution thereof.

In the compositions according to the invention, 2-(2'-hydroxyethylamino)-5-aminotoluene is preferably used as the sole developing agent in a proportion of about 0.05 to about 5% by weight, preferably 0.1 to 3 and most preferred 0.25 to 1.5% by weight, calculated to the total composition of the peroxide-free composition, and if present as a salt, calculated to the free base; in special cases, however, if a development of a particular shade is desired, the additional use of further developing agents in minor quantities is possible, e.g., p-phenylenediamine or p-toluylenediamine, 4-aminophenol, tetraaminopyrimidines or triaminohydroxypyrimidines.

Preferred coupling substances used in a preferred molar ratio of between about 1:1 and about 2.5:1 of developing agent to coupling substance are in particular:

Resorcinol, 2-methylresorcinol, 4-chlororesorcinol, 2-aminophenol, 4-(N-methyl)aminophenol, 3-aminophenol, 3-N,N-dimethylaminophenol, 4-amino-3-methylphenol, 5-amino-2-methylphenol, 6-amino-3-methylphenol, 3-amino-2-methylamino-6-methoxypyridine, 2-amino-3-hydroxypyridine, 4-aminodiphenylamine, 4,4'-diaminodiphenylamine, 2-dimethylamino-5-aminopyridine, 2,6-diaminopyridine, 1,3-diaminobenzene, 1-amino-3-(2'-hydroxyethylamino)benzene, 1-amino-3-[bis-(2'-hydroxyethyl)amino]benzene, 1,3-diaminotoluene, α-naphthol, 1,4-diamino-2-chlorobenzene, 4,6-dichlororesorcinol, 4-hydroxy-1,2-methylenedioxybenzene, 1,5-dihydroxynaphthalene, 1,7-dihydroxynaphthalene, 2,7-dihydroxynaphthalene, 1-hydroxynaphthalene, 4-hydroxy-1,2-methylenedioxybenzene, 2,4-diamino-3-chlorophenol, and (or) 1-methoxy-2-amino-4-(2'-hydroxyethylamino)benzene.

Obviously, mixtures of various coupling substances may be used to achieve special color shades, particularly mixtures of resorcinol or 2-methylresorcinol and 2-aminophenol and (or) 3-aminophenol, of resorcinol or 2-methylresorcinol and 1-methoxy-2-amino-4-(2'-hydroxyethylamino)-benzene, mixtures of 2-amino-3-hydroxypyridine and 5-amino-2-methylphenol and (or) 1-methoxy-2-amino-4-(2'-hydroxyethylamino)benzene, or, also, 1,3-diaminobenzene and 1,4-diamino-2-chlorobenzene.

Optionally, the usual direct dyestuffs may be added, e.g., the well-known Arianor dyestuffs or also nitro dyestuffs such as 2-amino-4,6-dinitrophenol, 2-amino-6-chloro-4-nitrophenol, 2-amino-4-nitrophenol, etc., as well as vegetable dyestuffs such as henna in minor quantities, i.e. between 0.05 and 1% by weight. Excluded is the addition of 2-nitro-p-phenylenediamine and 4-nitro-o-phenylenediamine due to the toxicologically hazardous properties thereof. The recommended total proportion of the dyestuff mixture in the final product is about 0.2 to about 6.0% by weight, preferably about 0.5 to about 4% by weight of the hair dye composition.

To prepare the hair dye composition according to the invention, the oxidation dyestuff presursors, i.e. the mixture of developing substance and coupling substance and optionally present dyestuffs, are incorporated in an acceptable cosmetic carrier. Preferably, such carriers are emulsions, i.e. creams, or gels.

These compositions and the other substances contained therein, particularly surface-active substances, stabilizers, thickeners etc. are well-known in the prior art and described in various publications such as the monography by K. Schrader, "Grundlagen und Rezepturen der Kosmetika", 2nd Edition (1989)., Hüthig Buchverlag, on pp. 796 to 815. Accordingly, this monography and others are expressly referred to and incorporated herein by reference.

Immediately before application, the compositions according to the invention are, in equal proportions, mixed with peroxide compounds, e.g., a 6% hydrogen peroxide solution, and applied to human hair, from where, after a processing time of about 15 to 30 minutes, the composition is washed out with water and a usual shampoo.

The hydrogen peroxide composition preferred per se may be substituted by other peroxide preparations, e.g. perborates, urea peroxide, melamin peroxide, etc.; however, since these preparations must be kept moisture-free, dosage and handling of this process are more complicated.

The following examples illustrate the invention.

EXAMPLES A-1 TO A-19

To a cream base comprising

| | |
|---|---|
| Cetylstearyl alcohol | 12.00% by wt. |
| Coconut monoethanolamide | 2.30 |
| Stearic acid monoethanolamide | 2.30 |
| Propyleneglycol monostearate | 0.60 |
| Oleyl alcohol ethoxylate (5 EO) | 5.00 |
| Oleic acid | 2.50 |
| 1,2-Propanediol | 1.00 |
| Sodium lauryl sulfate | 0.50 |
| Complexing agent (EDTA) | 0.50 |
| Ammonium chloride | 0.50 |
| Sodium sulfite | 0.50 |
| Ascorbic acid | 0.30 |
| Protein hydrolyzate | 1.00 |
| Perfume | 0.40 |
| Ammonia (25% solution) | 8.00 |
| Water | @ 100.00 | the following mixtures were added, marked in numerical order from 1 to 19 (proportions refer to percent by weight, calculated to the total composition each):

| | | % by wt. |
|---|---|---|
| No. 1: | 2-(2'-Hydroxyethylamino)-5-aminotoluene sulfate (subsequently called "E-1"):; | 0.536 |
| No. 2: | 1,7-Napthalenediol | 0.320 |
| | E-1 | 0.536 |
| | Resorcinol | 0.220 |
| | 4-Aminophenol | 0.100 |
| No. 3: | E-1 | 0.536 |
| | 3-Aminophenol | 0.218 |
| No. 4: | E-1 | 0.536 |
| | 3-N,N-Dimethylaminophenol | 0.274 |
| No. 5: | E-1 | 0.536 |
| | 5-Amino-2-methylphenol | 0.246 |
| No. 6: | E-1 | 0.536 |
| | 1-Methoxy-2-amino-4-(2'-hydroxyethyl-amino)benzene sulfate | 0.372 |
| No. 7: | E-1 | 0.536 |
| | 3-Amino-2-methylamino-6-methoxypyridine | 0.306 |
| No. 8: | E-1 | 0.536 |
| | 2-Amino-3-hydroxypyridine | 0.220 |
| No. 9: | E-1 | 0.536 |
| | 2-Dimethylamino-5-aminopyridine | 0.348 |
| No. 10: | E-1 | 0.536 |
| | 1-Naphthol | 0.288 |
| No. 11: | E-1 | 0.536 |
| | 2-Methylresorcinol | 0.248 |
| No. 12: | E-1 | 0.536 |
| | 2,6-Diaminopyridine | 0.218 |
| No. 13: | E-1 | 0.536 |
| | 2-Aminophenol | 0.218 |
| No. 14: | E-1 | 0.536 |
| | Resorcinol | 0.183 |
| | 3-Aminophenol | 0.036 |
| No. 15: | E-1 | 0.536 |
| | Resorcinol | 0.183 |
| | 1-Methoxy-2-amino-4-(2'-hydroxyethyl-amino)benzene sulfate | 0.061 |
| No. 16: | E-1 | 0.536 |
| | 5-Amino-2-methylphenol | 0.123 |
| | 2-Amino-3-hydroxypyridine | 0.110 |
| No. 17: | E-1 | 0.536 |
| | 2-Amino-3-hydroxypyridine | 0.183 |
| | 1-Methoxy-2-amino-4-(2'-hydroxyethyl-amino)benzene | 0.061 |
| No. 18: | E-1 | 0.536 |
| | 2-Methylresorcinol | 0.124 |
| | 2-Aminophenol | 0.110 |
| No. 19: | E-1 | 0.536 |
| | 2-Aminophenol | 0.146 |
| | 3-Aminophenol | 0.037 |
| | Resorcinol | 0.037 |

In each case, 20 g of these compositions were intensively mixed with 20 ml of 20% hydrogen peroxide solution, which mixtures had a pH-value of about 9.5; the compositions were applied onto the hair and after 30 minutes' processing time, it was rinsed, shampooed and dried. The following colorations were achieved:

| | |
|---|---|
| No. 1: | Rich blue |
| No. 2: | Rich golden brown |
| No. 3: | Rich smoke-colored grey |
| No. 4: | Rich olive-green |
| No. 5: | Rich violet |
| No. 6: | Rich dark blue |
| No. 7: | Rich bluish grey |
| No. 8: | Rich greyish violet |
| No. 9: | Rich greyish brown |
| No. 10: | Rich slightly red-tinged blue |
| No. 11: | Rich greyish brown |
| No. 12: | Rich turquoise |
| No. 13: | Rich brown olive |
| No. 14: | Rich ash shade |
| No. 15: | Rich steel grey |
| No. 16: | Rich aubergine |
| No. 17: | Rich light violet |
| No. 18: | Rich light grey |
| No. 19: | Rich greyish brown |

The color shades achieved were impressive particularly due to their expressive brilliance in comparison to traditional hair dye compositions based on customary developing agents.

EXAMPLES B-1 TO B-3

To a base comprising

| | |
|---|---|
| Cetylstearyl alcohol | 10.00% by wt. |
| Coconut fatty acid monoethanolamide | 1.60 |
| Stearic acid monoethanolamide | 2.20 |
| Oleic acid | 1.00 |
| Sodium lauryl sulfate | 0.50 |
| Ammonium chloride | 0.25 |
| Protein hydrolyzate | 0.60 |
| Perfume | 0.35 |
| Manganese(IV) oxide | 0.12 |
| Stabilizer, complexing agents | q.s. |
| Water | @ 100.00 |
| NaOH to adjust pH to 8.5 | | the following mixtures of developing/coupling substances were added, marked in numerical order from No. 1 to 3 (each in percent by weight, calculated to the total composition):

| | | % by wt. |
|---|---|---|
| No. 1: | 2-(2'-Hydroxyethylamino)-5-aminotoluene sulfate (subsequently called "E-1"), | 0.536 |
| | Resorcinol | 0.220 |
| | 2-Aminophenol | 0.040 |
| No. 2: | E-1 | 0.536 |
| | 3-Aminophenol | 0.218 |
| No. 3: | E-1 | 0.536 |
| | Resorcinol | 0.183 |
| | 3-Aminophenol | 0.036 |

20 g of each composition were intensively mixed with 40 ml each of 2% hydrogen peroxide solution, thereby achieving a pH value of about 6.8; the mixture was applied to the hair and, after 20 minutes' processing, the hair was rinsed with water, shampooed and dried.

The following colorful and bright shades were achieved.

| | |
|---|---|
| No. 1: | Pinkish brown |
| No. 2: | Smoke-colored grey |
| No. 3: | Pinkish grey. |

EXAMPLES C-1 AND C-2

To the basic composition described in example A was added:

| | | |
|---|---|---|
| No. 1: | 1.072% by wt. | 2-(2'-Hydroxyethylamino)-5-aminotoluene sulfate and a mixture of |
| No. 2: | 0.536% by wt. | 2-(2'-Hydroxyethylamino)-5-aminotoluene sulfate and |
| | 0.218% by wt. | 4-Aminophenol. |

Dyeing was performed as described in Example A.

In each case rich brown shades were obtained.

This proves that good hair dyeing results can also be achieved in the absence of coupling substances by using the developing agent according to the invention, alone or in admixture with another developing agent such as 4-aminophenol.

To achieve the desired color spectrum, an additional use of coupling substances, however, will normally be appropriate.

Skin irritation or sensitization have not been observed.

What is claimed is:

1. Peroxide-free hair dye compositions based on oxidation dyestuff precursors, which are mixable with a peroxide compound immediately before use, comprising at least one developing agent and at least one coupling agent, free from 1-methoxy-2, 4-diaminobenzene and 1-ethoxy-2,4diaminobenzene, wherein the composition contains one or both of 2-(2'-hydroxyethylamino)-5-aminotoluene and the salts thereof as substantially the sole developing agent, the 2-(2'-hydroxyethylamino)-5-aminotoluene being present at 0.05 to 5% by weight, calculated to a total composition of the peroxide-free composition and a free base, said coupling agent being selected from the group of resorcinol, 2-methylresorcinol, 4-chlororesorcinol, 2-aminophenol, 3-aminophenol, 4-(N-methylamino)phenol, 3-N-,N-dimethylaminophenol, 4-amino-3-methylphenol, 5-amino-2-methylphenol, 6-amino-3-methylphenol, 3-amino-2-methylamino-6-methoxypyridine, 2-amino-3-hydroxypyridine, 2-dimethylamino-5-aminopyridine, 2,6-diaminopyridine, 1-amino-3-(2'-hydroxyethylamino) benzene, 1-amino-3-[bis(2'-hydroxyethyl)amino]benzene, 1,3-diaminobenzene, 1,3-diaminotoluene, α-naphthol, 4-aminodiphenylamine, 4,4'-diaminodiphenylamine, 1,2-diaminobenzene, 1,4-diamino-2-chlorobenzene, 4,6-dichlororesorcinol, 4-hydroxy-1,2-methylenedioxybenzene, 1,5-dihydroxynaphthalene, 4-amino-1,2-methylenedioxybenzene, 1,7-dihydroxynaphthalene, 2,7-dihydroxynaphthalene, 2,4-diamino-3-chlorophenol, and 1-methoxy-2-amino-4-(2'-hydroxyethylamino) benzene.

2. Hair dye composition according to claim 1, wherein the composition contains as coupling agents a mixture of (a) one of resorcinol and 2-methylresorcinol and (b) one or both of 2-aminophenol and 3-aminophenol.

3. Hair dye composition according to claim 1, wherein the composition contains as coupling agents a mixture of (a) one of resorcinol and 2-methylresorcinol and (b) 1-methoxy-2-amino-4-(2'-hydroxyethylamino) benzene.

4. Hair dye composition according to claim 1, wherein the composition contains as coupling agents a mixture of (a) 2-amino-3-hydroxypyridine and (b) one or both of 5-amino-2-methylphenol and 1-methoxy-2-amino-4-(2'-hydroxyethylamino)benzene.

5. Hair dye composition according to claim 1, wherein the molar ratio of the developing agent to the coupling agent is from about 1:1 to 2.5:1.

6. Method of producing peroxide-free hair dye compositions based on oxidation dyestuff precursors, comprising (a) selecting one or both of 2-(2'-hydroxyethylamino)-5-aminotoluene and the salts thereof as substantially the sole developing agent, the 2-(2'-hydroxyethylamino)-5-aminotoluene being present at 0.05 to 5% by weight, calculated to a total composition of the peroxide-free composition and a free base, (b) selecting at least one coupling agent from the group of resorcinol, 2-methylresorcinol, 4-chlororesorcinol, 2-aminophenol, 3-aminophenol, 4-(N-methylamino)phenol, 3-N-,N-dimethylaminophenol, 4-amino-3-methylphenol, 5-amino-2-methylphenol, 6-amino-3-methylphenol, 3-amino-2-methylamino-6-methoxypyridine, 2-amino-3-hydroxypyridine, 2-dimethylamino-5-aminopyridine, 2,6-diaminopyridine, 1-amino-3-(2'-hydroxyethylamino) benzene, 1-amino-3-[bis(2'-hydroxyethyl)amino]benzene, 1,3-diaminobenzene, 1,3-diaminotoluene, α-naphthol, 4-aminodiphenylamine, 4,4'-diaminodiphenylamine, 1,2-diaminobenzene, 1,4-diamino-2-chlorobenzene, 4,6-dichlororesorcinol, 4-hydroxy-1,2-methylenedioxybenzene, 1,5-dihydroxynaphthalene, 4-amino-1,2-methylenedioxybenzene, 1,7-dihydroxynaphthalene, 2,7-dihydroxynaphthalene, 2,4-diamino-3-chlorophenol, and 1-methoxy-2-amino-4-(2'-hydroxyethylamino) benzene, (c) combining said developing agent and said coupling agent to form the hair dye composition, and (d) mixing said hair dye composition with a peroxide compound immediately before application.

* * * * *